(12) United States Patent
Stone et al.

(10) Patent No.: US 7,998,204 B2
(45) Date of Patent: Aug. 16, 2011

(54) COMPOSITE COLLAGEN MATERIAL AND METHOD OF FORMING SAME

(75) Inventors: Kevin T. Stone, Winona Lake, IN (US); Karen S. Troxel, Warsaw, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 529 days.

(21) Appl. No.: 11/833,115

(22) Filed: Aug. 2, 2007

(65) Prior Publication Data

US 2008/0021554 A1 Jan. 24, 2008

Related U.S. Application Data

(63) Continuation of application No. 11/010,836, filed on Dec. 13, 2004, now Pat. No. 7,252,832.

(51) Int. Cl.
*A61F 2/08* (2006.01)
*A61F 13/00* (2006.01)

(52) U.S. Cl. ............... 623/13.18; 623/14.12; 424/422

(58) Field of Classification Search .... 623/13.11–13.18, 623/14.12; 606/216
See application file for complete search history.

(56) References Cited

U.S. PATENT DOCUMENTS

| | | | |
|---|---|---|---|
| 4,501,029 A * | 2/1985 | McMinn | 623/13.18 |
| 4,772,288 A | 9/1988 | Borner et al. | |
| 4,834,734 A | 5/1989 | Morganti et al. | |
| 4,880,429 A * | 11/1989 | Stone | 623/14.12 |
| 5,067,964 A | 11/1991 | Richmond et al. | |
| 5,078,744 A | 1/1992 | Chvapil | |
| 5,116,373 A * | 5/1992 | Jakob et al. | 623/13.16 |
| 5,458,636 A | 10/1995 | Brancato | |
| 5,782,915 A | 7/1998 | Stone | |
| 5,866,165 A * | 2/1999 | Liu et al. | 424/486 |
| 6,050,979 A | 4/2000 | Haemmerle et al. | |
| 6,537,313 B2 | 3/2003 | Ketharanathan et al. | |
| 6,629,997 B2 * | 10/2003 | Mansmann | 623/14.12 |
| 2003/0114061 A1 * | 6/2003 | Matsuda et al. | 442/123 |
| 2003/0212456 A1 | 11/2003 | Lipchitz et al. | |
| 2004/0034418 A1 | 2/2004 | Li et al. | |

OTHER PUBLICATIONS

Cohn et al., Cardiac Surgery in the Adult, (New York: McGraw-Hill), 2003:15271536: Chapter 65, "Tissue engineering for cardiac surgery." See p. 9.

* cited by examiner

*Primary Examiner* — Bruce E Snow
*Assistant Examiner* — Melissa Hoban
(74) *Attorney, Agent, or Firm* — Harness, Dickey

(57) ABSTRACT

A felt for repairing soft tissue defects comprising a membranous collagen substrate and a bioresorbable fiber felted onto the collagen substrate. Methods of preparing a felt and methods of repairing soft tissue damage with a felt are also provided.

24 Claims, 4 Drawing Sheets

COMPOSITE COLLAGEN MATERIAL AND METHOD OF FORMING SAME

CROSS-REFERENCE TO RELATED APPLICATIONS

This application is a continuation of U.S. patent application Ser. No. 11/010,836 filed on Dec. 13, 2004 (now U.S. Pat. No. 7,252,832 issued Aug. 7, 2007). The disclosure of the above application is incorporated herein by reference.

FIELD

The present teachings relate to composite collagen materials. More particularly, the present teachings relate to a composite collagen felt used for soft tissue repair.

BACKGROUND

Collagen is useful in various pharmaceutical applications and as an implant material for soft tissue defects. The collagen useful for implant materials may be broadly categorized into xenograft collagen and allograft collagen. Selecting the appropriate collagen materials may present challenges as there is a need to balance strength and durability of the implant with reducing immunogenicity and promoting soft tissue ingrowth.

It may be desirable to provide an implant which promotes soft tissue ingrowth, minimizes the amount of the implant used, and is not prone to an immunogenic response.

SUMMARY

Embodiments of the present invention relate to felts for repairing soft tissue defects comprising a collagen substrate and a bioresorbable material felted onto the collagen substrate. The collagen substrate may be selected from a xenograft source, an allograft source, or a synthetic source. The collagen substrate may be from a porcine source. The collagen substrate may be uncrosslinked, partially crosslinked, or fully crosslinked. Chemical crosslinking may be introduced in an amount sufficient to make the collagen substantially non-bioactive. Bioresorbable materials may be selected from synthetic polymers, natural polymers, polysaccharides, and mixtures thereof. Synthetic polymers may include polymers and copolymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof. Natural polymers may include collagen, elastin, silk, fibrin, fibrinogen, or other naturally occurring tissue-derived proteins. Natural polysaccharides may include hyaluronic acid, chitin, chitosan, alginate, carboxymethylcellulose, or other polysaccharides. The felt may be substantially planar. The felt may also have nutrient factors, growth factors, antimicrobials, anti-inflammatory agents, blood products, autologous or allogeneic differentiated cells, autologous or allogeneic undifferentiated or stem cells, and mixtures thereof incorporated into the felt. Cartilage implants, ligament implants, or tendon implants are examples of what may be made with the felt.

Various embodiments of the present teachings relate to methods of augmenting a cartilage defect in need of soft tissue repair. A bioresorbable polymer in the form of a batting, web, or thread is felted onto a membranous collagen substrate to pass the bioresorbable polymer through the membranous collagen substrate. The felt is shaped to a predetermined shape to accommodate the cartilage defect and then implanted at the cartilage defect.

Still other various embodiments of the present teachings provide methods of augmenting a soft tissue defect. A felt is provided which includes a membranous collagen substrate and a bioresorbable polymer felted onto the substrate. The felt is shaped to provide at least a first attachment point and a second attachment point. The felt is then disposed at the soft tissue defect to encircle at least a region of a surrounding tissue at the soft tissue defect. The felt is affixed about the surrounding tissue at the soft tissue defect.

Further areas of applicability of the present teachings will become apparent from the detailed description provided hereinafter. It should be understood that the detailed description and specific examples, while indicating the preferred embodiment of the teachings, are intended for purposes of illustration only and are not intended to limit the scope of the teachings.

BRIEF DESCRIPTION OF THE DRAWINGS

The present teachings will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the teachings, their application, or uses. Although various embodiments may be illustrated in conjunction with a shoulder, elbow, or finger, it is understood that the felt and methods of the teachings may be of any appropriate shape and may be used with any appropriate procedure and not solely those illustrated.

Figure 1:
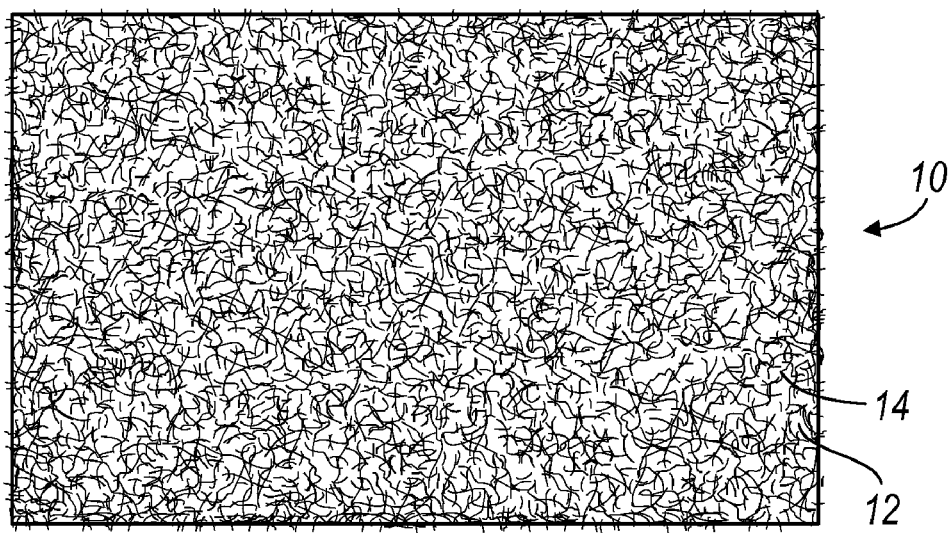
FIG. 1 depicts a felt according to embodiments of the present teachings.
Figure 2:
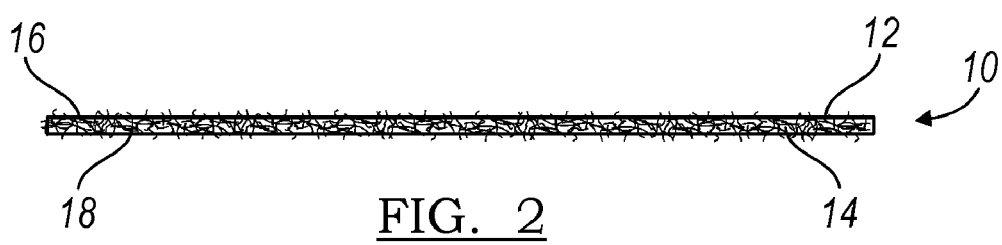
FIG. 2 depicts a cut away view of a felt according to embodiments of the present teachings.

As depicted in FIGS. 1 and 2, a felt 10 comprises a membranous collagen substrate 12 and a bioresorbable polymer 14 felted onto the substrate 12. The membranous collagen may be naturally derived from tissue such as submucosal intestine, or may be fabricated by casting a collagen solution into a membrane. The collagen substrate 12 may be from a xenograft source, an allograft source, or a synthetic source. For example, a porcine collagen may be used for the collagen substrate 12. Porcine collagen is readily available, provides flexibility of the collagen substrate 12, and is durable. Depending on the end use of the felt, the collagen substrate 12 may be from any collagen source (e.g. human, porcine, or bovine) which provides the desired durability, flexibility and permanence.

The collagen substrate 12 may uncrosslinked (0% linkages), partially crosslinked (greater than 0% and less than 100% linkages), or fully crosslinked (100% linkages). The collagen substrate 12 may be sufficiently crosslinked to be substantially non-resorbable and non-bioactive. One skilled in the art appreciates that the non-resorbtion or permanency of the collagen substrate 12 increases with the amount of crosslinked bonds. For example, in a highly crosslinked collagen substrate 12 having 85% crosslinked bonds, the collagen substrate 12 may remain implanted and substantially intact inside of a recipient for months, decades, or a lifetime. Furthermore, the high percentage of crosslinked bonds may ensure that the substantial majority of the collagen substrate 12 does not degrade, deform, or otherwise lose strength over the life of the implanted felt 10. In contrast, a lesser crosslinked collagen substrate 12 having about 10% linkage, may be for temporary use and designed to retain the majority of its structural integrity for only a few weeks or months. This may be useful in less load bearing areas of the body or in situations where the repair is minor and may be replaced with regenerated tissue in a short time period.

The bioresorbable polymer 14 may be a synthetic polymer, a natural polymer, polysaccharides, and mixtures thereof. Synthetic bioresorbable materials may include, but are not limited to, polymers and copolymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof. Other polymerizable hydroxy acids may also be employed. Synthetic resorbable materials may provide control in the amount of the material used as the benefits and delivery rates of the resorbable material 14 may be calculated based on known dissolution rates of the polymer. The bioresorbable polymer 14 may also be a natural polymer such as collagen, elastin, silk, fibrin, fibrinogen, other naturally occurring tissue-derived proteins, and mixtures thereof. Natural polysaccharides may include, without limitation, hyaluronic acid, chitin, chitosan, alginate, carboxymethylcellulose, other polysaccharides, and mixtures thereof. The bioresorbable polymer 14 collagen may be of the same or a different type or strength as the collagen substrate 12.

The bioresorbable polymer 14 may be a fluffy batting or web of threads of the linked monomers or the collagen. The fluffy batting forms a felt or dense cover over at least one of a top surface 16 and/or a bottom surface 18 of the collagen substrate 12. The dense cover may be of a random orientation or in a patterned form. The felt 10 may also include combinations of random and patterned orientations. The bioresorbable polymer 14 may be tightly felted to the surface of the collagen substrate 12 such that the fibers are touching or there is minimal space between each of the intertwined fibers. The tightness of the felt 10 may also be modified by having the bioresorbable polymer 14 fibers abut the top surface 16 and bottom surface 18 of the collagen substrate 12. The close fit between the bioresorbable polymer 14 and the collagen substrate 12 makes the felt 10 appear substantially planar when viewed from the side, as depicted in FIG. 2. The tightness of the felt 10 may be adjusted to incorporate additional elements into the substrate 12 or into the substrate 12 and the web of the bioresorbable polymer 14 such as autologous or allogeneic differentiated cells, autologous or allogeneic undifferentiated or stem cells and other biological agents, such as nutrient factors, growth factors, antimicrobials, anti-inflammatory agents, blood products, and mixtures thereof.

The bioresorbable polymer 14 resorbs faster than the collagen substrate 12 and elicits a positive tissue response to make newly generated tissues develop into the collagen substrate 12. The selection of bioresorbable polymers 14 may enhance the healing process. For example, it may be desirable to incorporate 65% of a slowly resorbing polymer 14 and 35% of rapidly resorbing polymer 14. The presence of the slowly resorbing polymer 14 may be used to enhance the strength of the felt 10 because the rapidly resorbing polymer 14 would initially elicit a tissue ingrowth response until it completely dissolved at which time the slowly resorbing polymer 14 would continue to promote ingrowth. The slowly resorbing polymer 14 may also provide enhanced strength to the felt 10 for a longer duration than a felt 10 containing a single bioresorbable polymer 14 or multiple bioresorbable polymers 14 having the same resorbtion rates.

Embodiments of the present teachings also provide methods of preparing the felt 10. A membranous collagen substrate 12 is provided. The collagen may be uncrosslinked or partially or fully crosslinked using, for example, chemical crosslinking, UV radiation, dehydrothermal crosslinking, and combinations of these treatments. Chemical crosslinking may be performed using a chemical crosslinking agent, including, but not limited to, carbodiimide, glutaraldehyde, formaldehyde, diisocyanates, and mixtures thereof. The crosslinking is carried out for a time and under conditions sufficient to provide a non-immunogenic collagen substrate 12. In embodiments where a greater degree of crosslinking is desired, the duration of the crosslinking treatment may increase or a successive series of crosslinking treatments (UV radiation followed by carbodiimide treatment, for example) may be used.

The felting process consists of using a barbed needle to pass the bioresorbable polymer 14 through a portion the collagen substrate 12. The barbs in the needle catch nearby bioresorbable polymer 14 fibers and mix, interlock, or weave them with other fibers to form the dense cover felt. The bioresorbable polymer 14 may be placed on the top surface 16, bottom surface 18, or both surfaces of the collagen substrate 12 to facilitate the felting process. The needle punches the bioresorbable polymer 14 through the top surface 16, into the collagen substrate 12, through the bottom surface 18, and back through the collagen substrate 12, or vice versa. The needle may also punch the resorbable polymer 14 through only a single surface of the collage substrate 12 without engaging the opposing surface. Repeating the felting punch or stitch provides a felt 10 with bioresorbable polymer 14 covering a single surface or both surfaces of the collagen substrate 12.

Selection of the felting needle may influence the final porosity of the collagen substrate 12. Needles may be selected for shaft type (conical, square, star, or triangular), gauge, and the number of barbs on the needle. For example, a felt 10 created with a 20-gauge needle has a greater pore size after the bioresorbable polymer 14 resorbs, as compared to the pore size created by a 32-gauge needle. The pores and indentations created by the shaft shape and barbs may be exploited to maximize tissue ingrowth and thereby increase the strength of the implant in the body. The needle barb number, needle gauge size, the placement of the bioresorbable polymer 14 on the collagen substrate 12, and the extent of the punching process may be altered to provide a tight felt 10 with closely felted fibers.

After the felting process, the felt 10 may be treated to increase compatibility in the body. The felt 10 may be sterilized using radiation, for example. Agents to increase ingrowth of tissues into the collagen substrate 12 may also be applied to the felt 10, such as nutrient factors, growth factors, antimicrobials, anti-inflammatory agents, blood products, autologous or allogeneic differentiated cells, autologous or allogeneic undifferentiated or stem cells, and mixtures thereof.

Figure 3:
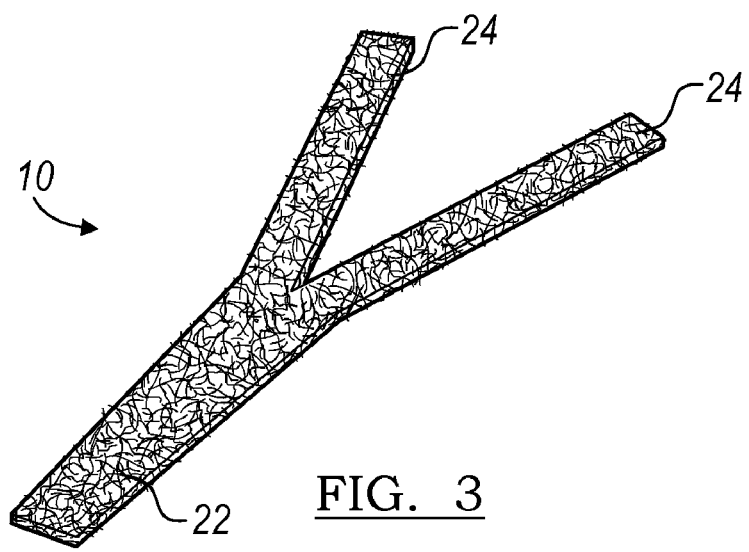
FIG. 3 depicts a bifurcated felt according to embodiments of the present teachings.
Figure 4A:
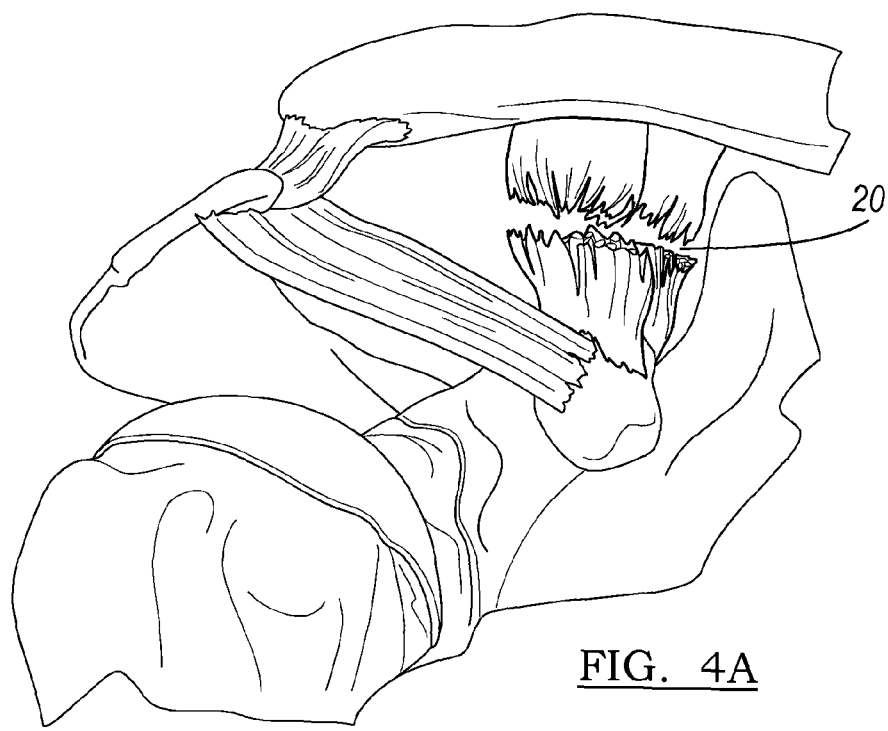
FIGS. 4A-4B depict a torn coracoclavicular ligament repaired with a felt according to embodiments of the present teachings.
Figure 4B:
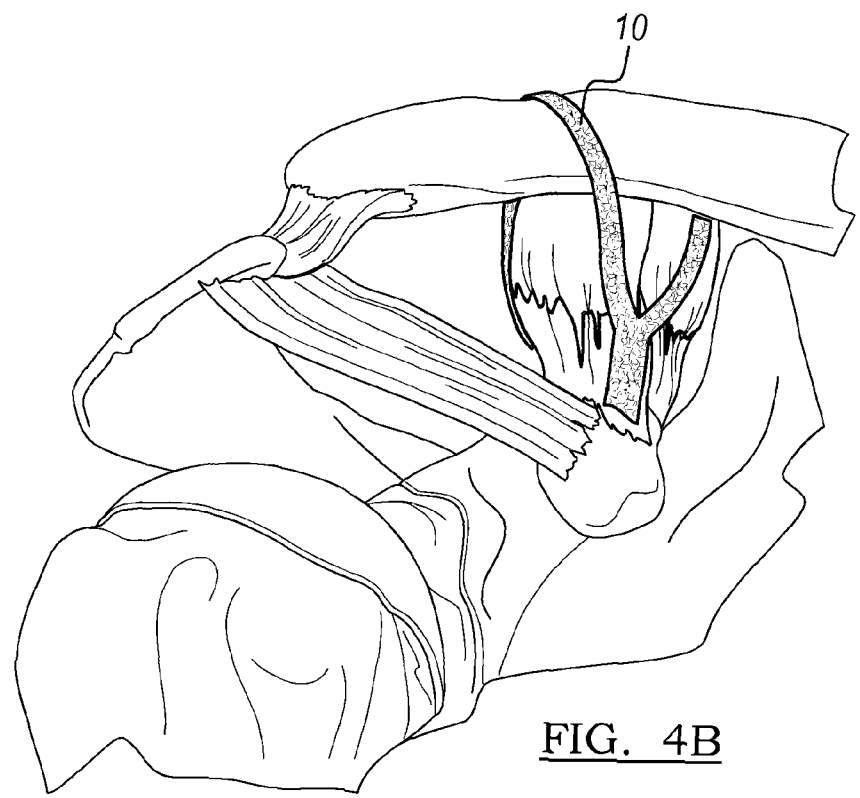

Various embodiments of the present teachings may be used to augment a site in need of soft tissue repair 20. The felts 10 of embodiments of the teachings are placed at a site in need of soft tissue repair 20. If needed, the felts 10 may be shaped prior to use. For example, the felt 10 may be shaped into a bifurcated strip having a base 22 and prongs 24, as depicted in FIG. 3. The bifurcated shape (or trifurcated, etc.) may be useful in augmenting sites by attaching the base 22 to one area in need of repair 20 and the prongs 24 to another area in need of repair 20 or by looping at least one of the prongs 24 around the site in need of repair 20. As depicted in FIG. 4A, an injury to the acromioclavicular ligament, coracoclavicular ligament, or the coracoacromial ligaments in the shoulder may cause displacement of the clavicle. A bifurcated felt 10 of the present teachings may be used to reduce the clavicle to the appropriate level by attaching the base 22 to the coracoid process and attaching the prongs 24 to the coracoclavicular ligament. The prongs 24 may also be looped around the clavicle or in the case of the clavicle having a drill hole therein (not depicted), looped through the clavicle to reduce it to the appropriate level. The felt 10 may be attached using any suitable attachment means such as sutures, screws, staples, etc.

Figure 5A:
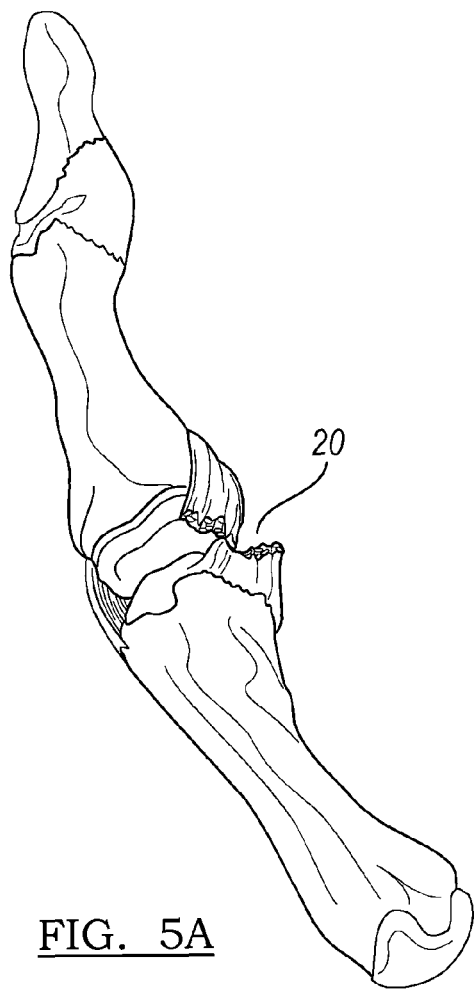
FIGS. 5A-5B depict a torn ulnar collateral ligament repaired with a felt according to embodiments of the present teachings.
Figure 5B:
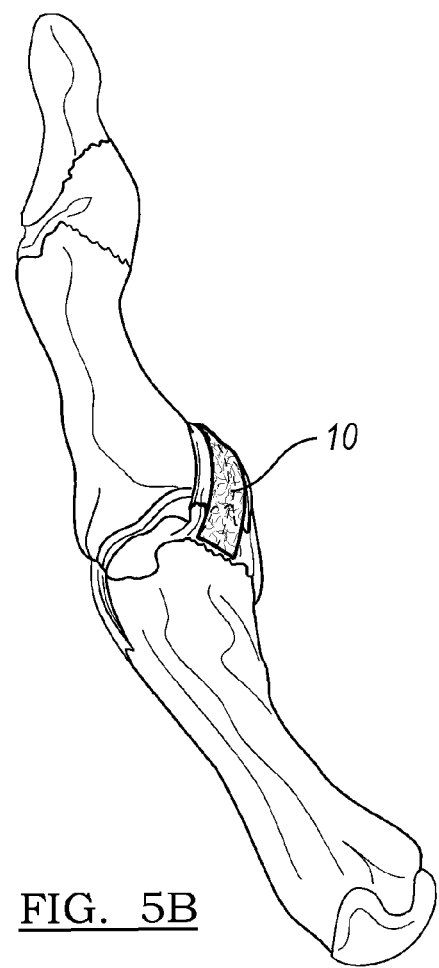
Figure 6A:
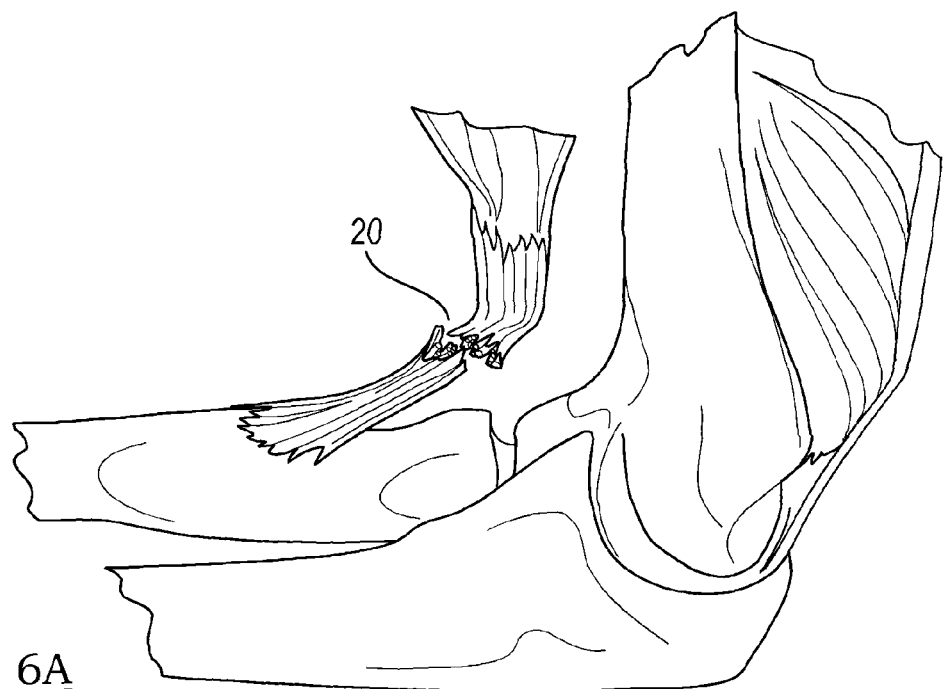
FIGS. 6A-6B depict a torn biceps tendon repaired with a felt according to embodiments of the present teachings.
Figure 6B:
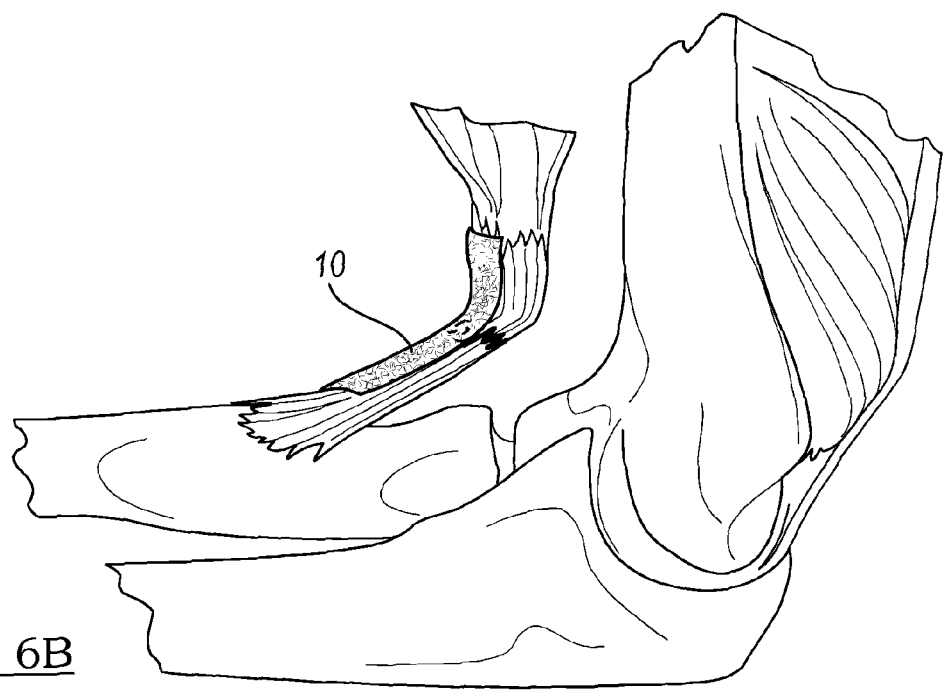

The methods may also be used in other regions of the body. Referring to FIGS. 5A and 5B, the site in need of repair 20 is a torn ulnar collateral ligament of the thumb. In such an embodiment a small felt 10 may be used to create a bridge between the torn tissues. As depicted in FIGS. 6A and 6B, the site in need of repair 20 is a torn biceps tendon which may also be repaired with the felt 10 bridging the two torn pieces of the biceps tendon. It is understood that the methods of the present teachings may be employed in various areas of the body, including knees, wrists, ankles, etc.

The description of the teachings is merely exemplary in nature and, thus, variations that do not depart from the gist of the teachings are intended to be within the scope of the teachings. Such variations are not to be regarded as a departure from the spirit and scope of the teachings.

What is claimed is:

1. A felt for repairing a defect comprising:
   a. a membranous collagen substrate shaped to accommodate the defect, wherein the defect is one of a tendon defect, a cartilage defect, and a ligament defect; and
   b. a bioresorbable material felted onto the collagen substrate such that the bioresorbable material extends through the membranous collagen substrate from a top side of the membranous collagen substrate to a bottom side of the membranous collagen substrate that is opposite to the top side, the bioresorbable material is formed as one of a batting and a plurality of threads,
   wherein the bioresorbable material is selected from the group consisting of: a synthetic polymer, a natural polymer, a polysaccharide, and combinations thereof.

2. The felt according to claim 1, wherein the felt provides a bridge between tissue at the defect.

3. The felt according to claim 1, wherein the felt provides multiple attachment points to secure the felt at the defect.

4. The felt according to claim 1, wherein the felt is bifurcated.

5. The felt according to claim 1, wherein the synthetic polymer is selected from the group consisting of: polymers and co-polymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof; the natural polymer is selected from the group consisting of: elastin, silk, fibrin, fibrinogen, and mixtures thereof; and the polysaccharide is selected from the group consisting of: hyaluronic acid, chitin, chitosan, alginate, carboxymethylcellulose, and mixtures thereof.

6. The felt according to claim 1, wherein the bioresorbable material is felted on to the membranous collagen substrate in an order selected from the group consisting of: a patterned form, a random orientation, and combinations thereof.

7. The felt according to claim 1, further comprising a member selected from the group consisting of: differentiated stem cells, undifferentiated stem cells, nutrient factors, growth factors, antimicrobials, anti-inflammatory agents, blood products, and mixtures thereof.

8. A felt for repairing a defect comprising:
   a. a membranous collagen substrate having a top surface and a bottom surface that is opposite to the top surface; and
   b. a bioresorbable material felted onto the collagen substrate such that the bioresorbable material is stitched in only one of the top surface or the bottom surface, the bioresorbable material includes at least one of a synthetic polymer, a natural polymer, and a polysaccharide,
   wherein the felt provides a bridge to repair a defect site selected from the group consisting of: a tendon, a cartilage, or a ligament.

9. The felt according to claim 8, wherein the defect site is at a tendon and further wherein the tendon comprises a biceps tendon.

10. The felt according to claim 8, wherein the defect site is at a ligament and further wherein the ligament comprises a ligament in a hand or a wrist.

11. The felt according to claim 8, wherein the defect site is a ligament and the felt has a substantially Y-shape to accommodate a clavicular ligament repair.

12. The felt according to claim 8, wherein the defect site is at a cartilage site.

13. The felt according to claim 8, wherein an entirety of the bioresorbable material is stitched in the collagen substrate.

14. The felt according to claim 8, wherein the bioresorbable material is stitched in an entirety of the top surface of the collagen substrate, the top surface is an exterior surface of the collagen substrate.

15. The felt according to claim 8, wherein the bioresorbable material extends entirely across the top surface of the collagen substrate, the top surface is an exterior surface of the collagen substrate.

16. The felt according to claim 8, wherein the bioresorbable material covers the top surface of the collagen substrate, the top surface is an exterior surface of the collagen substrate.

17. A felt for repairing a defect comprising:
   a membranous collagen substrate shaped to accommodate at least one of a tendon defect, cartilage defect, or a ligament defect;
   a bioresorbable material that is felted onto the collagen substrate such that it is woven into and interlocked on the collagen substrate, and extends through the collagen substrate from a top surface to a bottom surface of the collagen substrate, including at least one of a synthetic polymer, a natural polymer, and a polysaccharide; and
   a member selected from the group consisting of: differentiated stem cells, undifferentiated stem cells, nutrient factors, growth factors, antimicrobials, anti-inflammatory agents, blood products, and mixtures thereof;
   wherein the felt provides a bridge to repair one of a tendon, a cartilage, or a ligament.

18. The felt of claim 17, wherein the bioresorbable material includes a plurality of different materials.

19. The felt of claim 17, wherein the synthetic polymer is selected from the group consisting of: polymers and co-polymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof;
   wherein the natural polymer is selected from the group consisting of: elastin, silk, fibrin, fibrinogen, and mixtures thereof; and
   wherein the polysaccharide is selected from the group consisting of: hyaluronic acid, chitin, chitosan, alginate, carboxymethylcellulose, and mixtures thereof.

20. The felt of claim 17, wherein the felt is generally Y-shaped to accommodate a clavicular ligament repair.

21. The felt of claim 17, wherein the felt is bifurcated.

22. The felt of claim 17, wherein the felt provides a bridge between tissue at a defect site.

23. The felt of claim 17, wherein the felt provides multiple attachment points to secure the felt at a defect site.

24. The felt of claim 17, wherein the tendon is a biceps tendon.

* * * * *

UNITED STATES PATENT AND TRADEMARK OFFICE
CERTIFICATE OF CORRECTION

| | |
|---|---|
| PATENT NO. | : 7,998,204 B2 |
| APPLICATION NO. | : 11/833115 |
| DATED | : August 16, 2011 |
| INVENTOR(S) | : Kevin T. Stone and Karen S. Troxel |

It is certified that error appears in the above-identified patent and that said Letters Patent is hereby corrected as shown below:

Column 2, line 64, after "may", insert --be--.

Column 4, line 27, after "portion", insert --of--.

Column 4, line 38, "collage" should be --collagen--.

Signed and Sealed this
Eighth Day of November, 2011

David J. Kappos
*Director of the United States Patent and Trademark Office*